US007226558B2

(12) United States Patent
Nieman et al.

(10) Patent No.: US 7,226,558 B2
(45) Date of Patent: Jun. 5, 2007

(54) METHOD OF MAKING AN EXPANDED POLYTETRAFLUOROETHYLENE STRUCTURE

(75) Inventors: Tim Nieman, Chandler, AZ (US); Randy Earl Saylor, Gilbert, AZ (US); Robert Hunkins, Mesa, AZ (US); Robert Calcote, Issaquah, WA (US)

(73) Assignee: Bard Peripheral Vascular, Inc., Tempe, AZ (US)

( * ) Notice: Subject to any disclaimer, the term of this patent is extended or adjusted under 35 U.S.C. 154(b) by 243 days.

(21) Appl. No.: 10/772,915

(22) Filed: Feb. 5, 2004

(65) Prior Publication Data

US 2004/0164445 A1    Aug. 26, 2004

Related U.S. Application Data

(62) Division of application No. 09/718,923, filed on Nov. 22, 2000, now abandoned.

(51) Int. Cl.
*B28B 11/08* (2006.01)
*B29C 55/00* (2006.01)
*B28B 5/00* (2006.01)

(52) U.S. Cl. .............. 264/291; 264/294; 264/211.12; 264/175; 264/635; 264/566; 425/363; 425/374; 425/383; 425/364 R; 623/901

(58) Field of Classification Search ......... 425/374, 425/364 R, 383; 623/901; 264/566, 503
See application file for complete search history.

(56) References Cited

U.S. PATENT DOCUMENTS

| 3,027,601 A | 4/1962 | Barry |
| 3,085,290 A | 4/1963 | Chu |
| 3,234,311 A | 2/1966 | Pratt et al. |
| 3,953,566 A | 4/1976 | Gore |
| 4,177,334 A | 12/1979 | Okita |
| 4,187,390 A | 2/1980 | Gore |
| 4,203,938 A | 5/1980 | Burnett et al. |
| 4,209,480 A | 6/1980 | Homsy |
| 4,248,924 A | 2/1981 | Okita |
| 4,250,138 A | 2/1981 | Okita |
| 4,277,429 A | 7/1981 | Okita |
| 4,482,516 A | 11/1984 | Bowman et al. |
| 4,598,011 A | 7/1986 | Bowman |
| 4,743,480 A | 5/1988 | Campbell |
| 4,877,661 A | 10/1989 | House et al. |

(Continued)

FOREIGN PATENT DOCUMENTS

EP    0 313 263    4/1989

(Continued)

OTHER PUBLICATIONS

Declaration of Tim Nieman (w/ Exhibit 1).

(Continued)

*Primary Examiner*—Christina Johnson
*Assistant Examiner*—Jeff Wollschlager
(74) *Attorney, Agent, or Firm*—Morrison & Foerster LLP

(57) ABSTRACT

A high density microwall ePTFE structure and a method for making, involving the manipulation of a standard extruded ePTFE graft. The final product has the desired characteristics of high density, reduced wall-thickness, above-average radial strength and enhanced suture retention.

14 Claims, 4 Drawing Sheets

U.S. PATENT DOCUMENTS

| | | |
|---|---|---|
| 4,955,899 A | 9/1990 | Della Corna et al. |
| 4,961,891 A | 10/1990 | Pitolaj |
| 4,985,296 A | 1/1991 | Mortimer, Jr. |
| 5,026,513 A | 6/1991 | House et al. |
| 5,207,960 A * | 5/1993 | Moret de Rocheprise .. 264/103 |
| 5,308,664 A | 5/1994 | House et al. |
| 5,321,109 A | 6/1994 | Bosse et al. |
| 5,374,473 A | 12/1994 | Knox et al. |
| 5,514,231 A | 5/1996 | Thomas |
| 5,677,047 A | 10/1997 | Thomas |
| 5,708,044 A | 1/1998 | Branca |
| 5,827,327 A | 10/1998 | McHaney et al. |
| 6,016,848 A * | 1/2000 | Egres, Jr. .................... 138/137 |
| 6,187,054 B1 * | 2/2001 | Colone et al. .............. 128/898 |
| 6,402,779 B1 | 6/2002 | Colone et al. |
| 6,436,135 B1 | 8/2002 | Goldfarb |
| 6,638,468 B1 | 10/2003 | Hill et al. |
| 2002/0183716 A1 * | 12/2002 | Herweck et al. ............ 604/509 |

FOREIGN PATENT DOCUMENTS

| | | |
|---|---|---|
| EP | 0 391 586 | 10/1990 |
| WO | WO 98/33453 | 8/1998 |
| WO | WO 00/45739 | 8/2000 |
| WO | WO 01/06953 A1 | 2/2001 |

OTHER PUBLICATIONS

Declaration of Scott Randall.

* cited by examiner

METHOD OF MAKING AN EXPANDED POLYTETRAFLUOROETHYLENE STRUCTURE

CROSS-REFERENCE TO RELATED APPLICATIONS

This application is a divisional of application Ser. No. 09/718,923, filed Nov. 22, 2000 now abandoned, which is expressly incorporated by reference as if fully set forth herein.

STATEMENT REGARDING FEDERALLY SPONSORED RESEARCH OR DEVELOPMENT

Not applicable.

REFERENCE TO A COMPACT DISK APPENDIX

Not applicable.

BACKGROUND OF THE INVENTION

This invention relates generally to biocompatible materials useful in the field of medical devices, and more particularly to expanded polytetrafluoroethylene (hereinafter "ePTFE") material with a combination of improved properties, including mechanical strength and reduced thickness, and a method for producing this material.

The highly functional ePTFE material is used for numerous different purposes in the medical field. One of the most prominent uses is to encapsulate a stent made of metal between two layers of ePTFE. The ePTFE provides the metal stent with a covering, which enables the patency of the device as well as providing a more laminar flow of blood through the device. In addition, ePTFE material expands and contracts with the stent, allowing greater flexibility in introducing the device into a body and in deploying the device at a desired location.

The ePTFE material is advantageous for medical use because of its healing properties due to a porous microstructure. This microstructure consists of spaced apart nodes and fibrils, which permits the transmural migration of capillaries through its matrix. Additional advantages of ePTFE over other biocompatible materials used in the medical industry are the expandability and recovery characteristics of the ePTFE as well as its relative compliance and patency. In addition, ePTFE can be manipulated to accentuate many of its desired attributes. For instance, ePTFE can be made more porous to further promote healing characteristics, or can be made more expandable to promote compliance aspects.

The ePTFE material is advantageous for medical use because of its healing properties due to a porous microstructure. This microstructure consists of spaced apart nodes and fibrils, which permits the transmural migration of capillaries through its matrix. Additional advantages of ePTFE over other biocompatible materials used in the medical industry are the expandability and recovery characteristics of the ePTFE as well as its relative compliance and patency. In addition, ePTFE can be manipulated to accentuate many of its desired attributes. For instance, ePTFE can be made more porous to further promote healing characteristics, or can be made more expandable to promote compliance aspects.

Strength is another quality of ePTFE that can be enhanced through manipulation of the material. The strength of the ePTFE is very important because of the difficulties and invasiveness of multiple surgeries. Lack of material strength could result in its tearing or ripping, which would necessitate frequent replacing of the device. Thus it is often desired to improve the strength component of ePTFE through manipulation of the material. This is especially true for single layer ePTFE grafts that are utilized to create a skin around an implantable structural support device, such as a stent. In many cases, conventional ePTFE grafts of sufficient strength to operate effectively as a single tubular layer possess a profile or wall thickness that is far too thick for percutaneous delivery. Thus, when overall profile of the implanted device is a leading consideration, a single layer ePTFE graft must be provided with a very small wall thickness, yet be strong enough to maintain its patency under adverse conditions. Up until now, there has not been disclosed a method of producing such a material.

Consequently, there exists the need for an ePTFE material with a reduced profile that has significantly improved strength characteristics compared to similarly sized prior art material, and a method for producing the same.

BRIEF SUMMARY OF THE INVENTION

Accordingly, the present invention provides a high density microwall ePTFE structure with increased radial strength and suture retention strength and a method for producing the same. The inventive high density microwall ePTFE is remarkable in that the aforementioned properties are achieved in combination with a sizeable reduction in the ePTFE's thickness, whether it be in the form of a graft or other implantable device. In addition, due to the reduction in wall thickness and resulting increase in density, the high density microwall ePTFE has a lower percentage porosity than prior art ePTFE materials with similar internodal distances.

The method of manufacture involves the manipulation of a standard extruded ePTFE graft, or one that has already undergone longitudinal expansion and been sintered. The standard graft is placed within a restraining tube and is balloon dilated to approximately four times its original diameter. The radially dilated ePTFE is then placed onto a like-sized mandrel such that an interference fit is maintained. This loaded mandrel is placed into a calendering device consisting of two metal plates, where a force is applied to the top plate and the bottom plate is moved reciprocally along a direction perpendicular to the central axis of the mandrel. After the rolling motion and compression of the entire graft wall is complete, the loaded mandrel is placed into a heated furnace or oven at a temperature above the crystalline melt-point for PTFE for a pre-determined time. This process in conjunction with the calendering is critical to provide the increased strength characteristics in the final product. The final product has the desired characteristics of high density, reduced wall-thickness, above-average radial strength and enhanced suture retention. These physical properties are variable depending on the compression or calendering parameters of the graft and the parameters of the second sintering cycle.

These and other features and advantages of the present invention will become more apparent to those skilled in the art when taken with reference to the following more detailed description of the preferred embodiments of the invention and the accompanying drawings.

DETAILED DESCRIPTION OF THE INVENTION

The following detailed description should be read with reference to the drawings, in which like elements in different drawings are identically numbered. The drawings, which are not necessarily to scale, depict selected preferred embodiments and are not intended to limit the scope of the invention. The detailed description illustrates by way of example, not by way of limitation, the principles of the invention. This description will clearly enable one skilled in the art to make and use the invention, and describes several embodiments, adaptations, variations, alternatives and uses of the invention, including what is presently believed to be the best mode of carrying out the invention.

The present invention satisfies the need for a thin-walled ePTFE implantable device that has superior strength qualities. This is satisfied by the high density microwall (HDM) ePTFE material of the present invention. This material has been tested for all of the standard strength properties, including water entry pressure (WEP), radial tensile strength (RTS), suture retention strength (SRS) and longitudinal maximum load (LML), and has returned superior performance results. The truly unique characteristic of the present invention is that the strength characteristics are improved while the profile of the material is significantly reduced.

Figure 1:
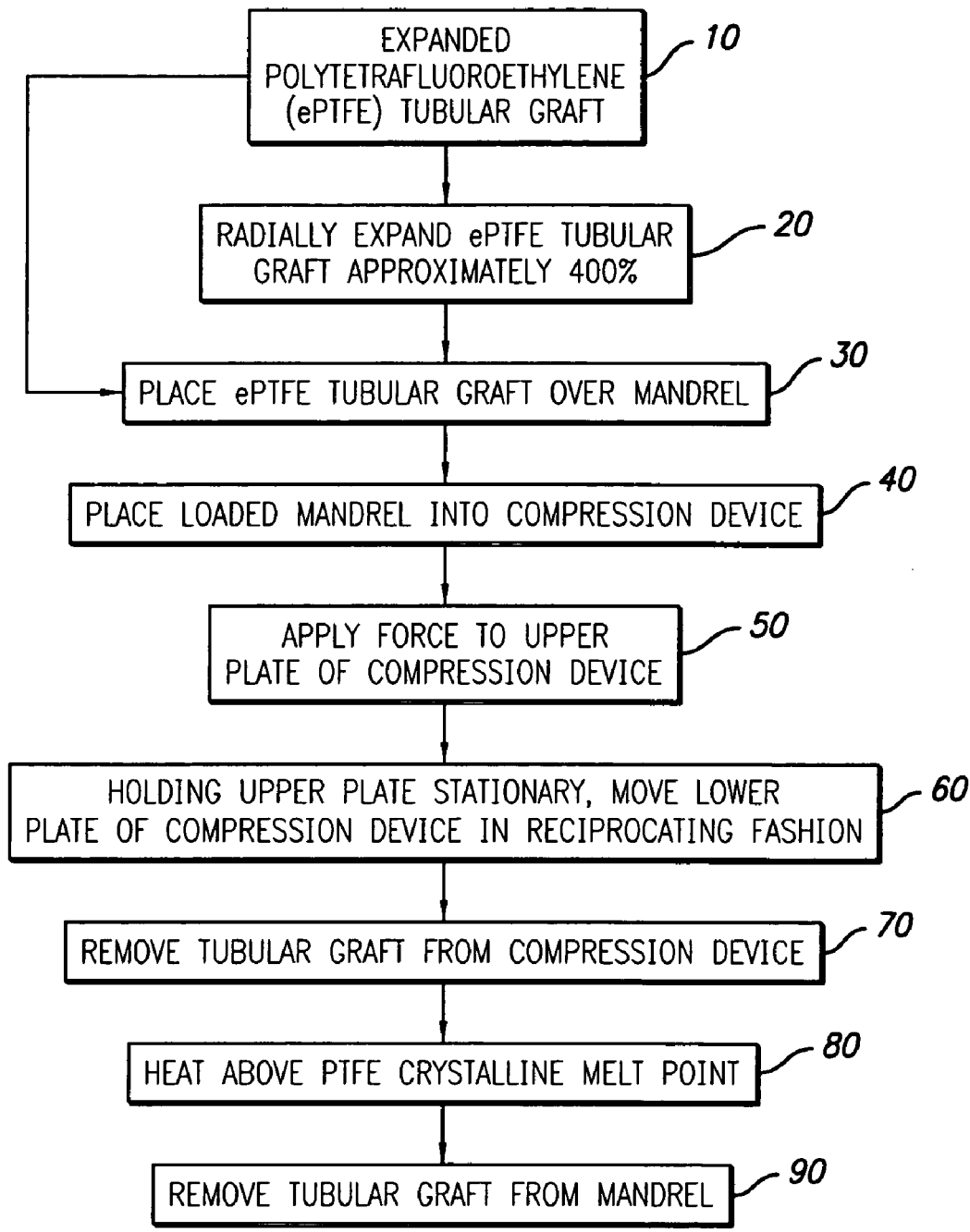
FIG. 1 is a flow chart describing the basic process of the present invention.

FIG. 1 refers to the general process steps for producing a tubular structure according to the present invention. A standard ePTFE tubular graft is provided in step 10. This graft is one that has been extruded, expanded longitudinally and sintered by a method such as the one described in U.S. Pat. No. 5,321,109, which is incorporated by reference herein. The ePTFE tubular graft may be placed directly onto a mandrel for processing in step 30 or may first be radially expanded in step 20. In the preferred embodiment, the ePTFE tubular graft is first positioned over a balloon and placed within a restraining tube for radial dilation in step 20. The restraining tube restricts the expansion of the ePTFE tubular graft in the radial direction, and can be set at any desired radius. It has been discovered after much experimentation that an expansion of approximately 400% of the original diameter is optimal for producing the best strength results. Once the radial expansion has been completed, the ePTFE tubular graft is pulled over a mandrel (metal cylindrical object) of similar diameter and greater length to provide an interference fit between the two objects in step 30, creating a "loaded mandrel."

Figure 2:
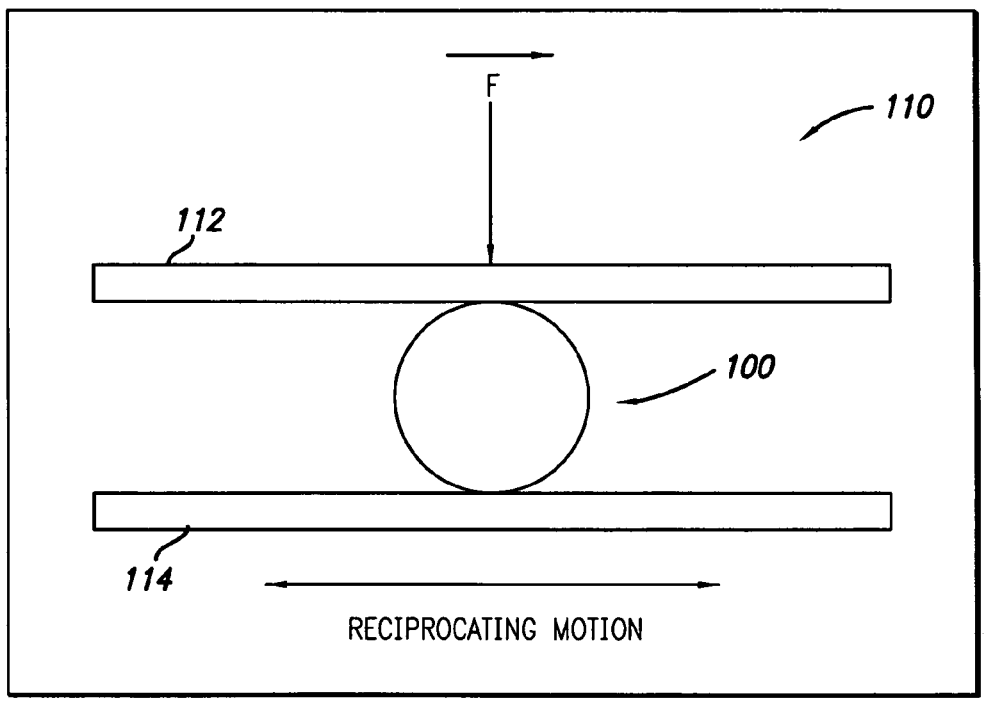
FIG. 2 is an end view of a simplified depiction of the calendering step of the present invention.

The loaded mandrel 100, as seen in FIG. 2, is placed into a calendering device 110, which in the preferred embodiment consists of opposing parallel first and second plates 112 and 114; however, it should be appreciated by one of skill in the art that many other devices can be used to produce similar results. The loaded mandrel 100 is positioned between first and second plates 112 and 114 and the respective plates are kept in parallel relation to one another. In an alternate embodiment, a secondary plate, or other sheet of material is placed between the loaded mandrel 100 and either one or both of the plates as a processing aid to provide a cushion for the loaded mandrel 100. In step 50 (see FIG. 1), a force is applied to the first plate 112, while the parallel relationship to the respective plates is maintained, placing the loaded mandrel 100 in compression. As the first plate 112 is held stationary, the second plate 114 is moved in reciprocating fashion in directions perpendicular to the force 120 applied to first plate 112 so that the entire wall of the ePTFE tubular graft is calendered between the mandrel and the respective plates 112 and 114 in step 60. As one skilled in the art can appreciate, there are many variations possible in the calendering of the ePTFE tubular graft wall in accordance with the present invention. For instance, the force applied to the first plate 112, the number of reciprocal cycles performed, and stroke distance (length that the second plate 114 is moved in one direction relative to the starting point) are all variables that can be altered depending on the product type and the physical properties sought to be optimized.

After sufficient calendering of the ePTFE tubular graft wall has taken place, the loaded mandrel 100 is removed from the calendering device 110 and placed into a furnace, oven or other heating apparatus where it is heated above the crystalline melt point of PTFE in step 80 for a sufficient time to ensure that the entire structure is raised above this crystalline melt point. Once the heating cycle is complete, the graft is carefully removed from the mandrel in step 90.

Figure 3:
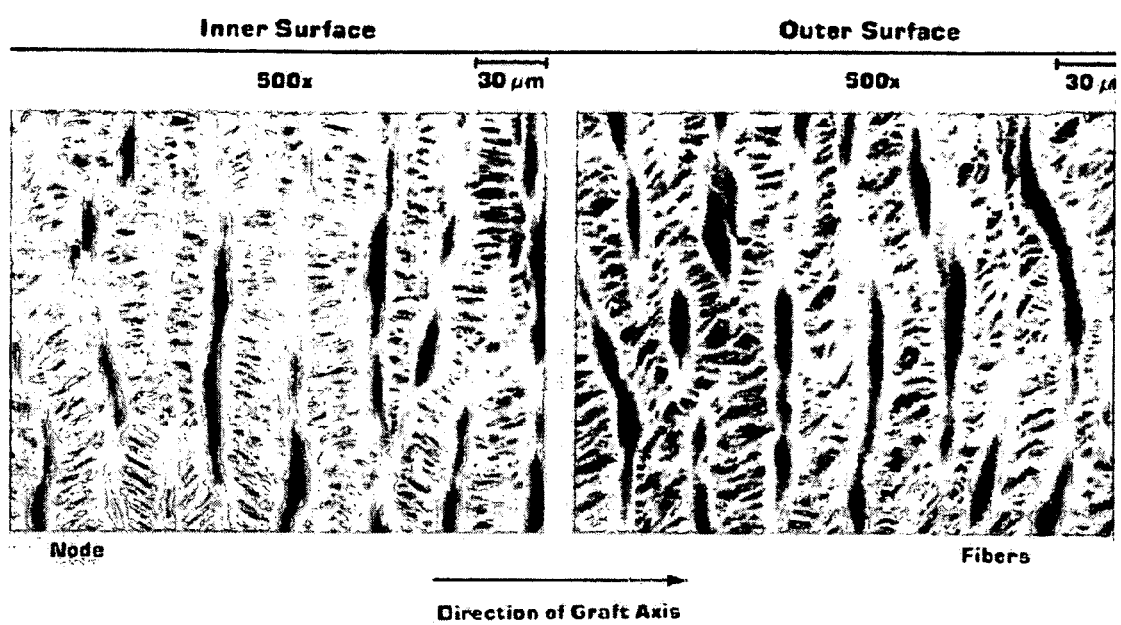
FIG. 3 is a photomicrograph of the inner and outer surfaces of a prior art ePTFE graft.
Figure 4:
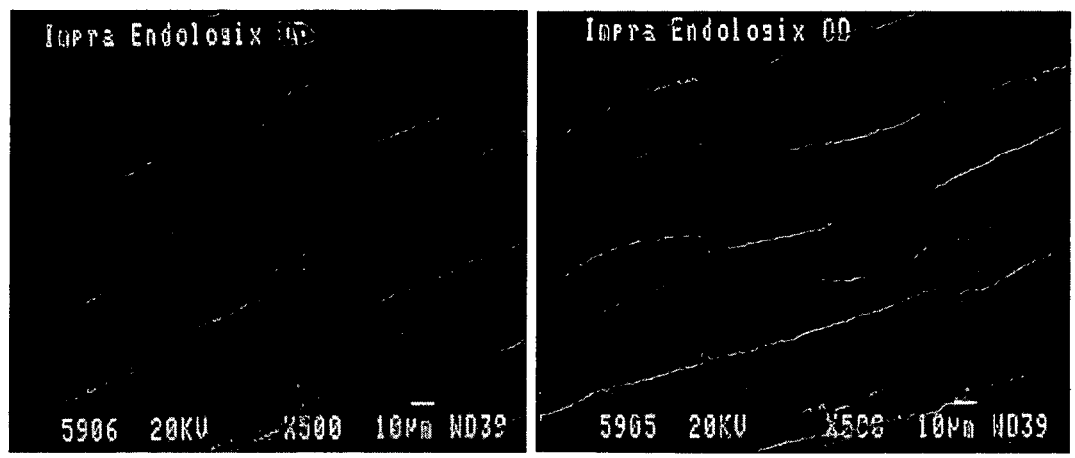
FIG. 4 is a photomicrograph of the inner and outer surfaces of a high density ePTFE graft.

The difference in density between a prior art ePTFE graft and an HDM ePTFE graft made according to the present invention is illustrated in FIGS. 3 and 4. FIG. 3 is a photomicrograph of both the inner and outer surfaces of a prior art ePTFE graft, taken at 500 magnification. What is seen in these photomicrographs are the nodes (parallel thick white lines) interconnected by fibrils (horizontal web-like lines). FIG. 4, on the other hand, is the same magnification of both inner and outer surfaces of a HDM ePTFE graft. It is apparent from this view just how dense the HDM material is in comparison to the prior art material, because the fibrils are barely noticeable. As one can appreciate, these highly compacted walls of the HDM material result in a much less porous structure than the prior art graft, even though the two may have identical internodal distances. Thus, yet another advantage is realized by the HDM ePTFE material of the present invention because it can be used for applications calling for very low porosity percentage without having to further manipulating the internodal distances of the material.

Table 1 (see below) provides another contrast between prior art ePTFE grafts and the HDM material of the present invention by comparing standard strength measurements. These properties were discovered through extensive testing and have been re-confirmed on several occasions.

TABLE 1

Comparison of Prior Art ePTFE Grafts and HDM Grafts

| Physical Property | Prior Art ePTFE | | HDM | |
| --- | --- | --- | --- | --- |
| | Range | Average | Range | Average |
| Wall Thickness (mm) | 0.15–4.0 | 0.5 | 0.075–0.30 | 0.09 |
| IND (microns) | 10–30 | 13 | 10–30 | 13 |
| WEP (psi) | 4–7 | 5 | 7–15 | 10 |
| RTS (N/mm) | 3.3–8.9 | 5 | 5–15 | 10 |
| LML (N) | 133–230 | 170 | 130–300 | 260 |
| SRS (g) | 200–250 | 230 | 200–900 | 560 |
| Burst (psi) | 28–40 | 35 | 20–40 | 30 |

As this data illustrates, the HDM ePTFE grafts produced according to the present invention are remarkably strong and have strength characteristics equivalent or better than grafts with a much larger wall thickness. In particular, the HDM material provides a much stronger SRS (maximum force required to pull a 6-0 prolene suture through the graft wall with a 2 mm suture bite), RTS (the circumferential strength measured as a break force over the area of an applied load), LML (maximum tensile load in the longitudinal axis), as well as higher WEP values (the pressure at which the hydrophobic barrier is broken, allowing migration of water through the wall of the graft) than that obtainable for prior art ePTFE with an equivalent wall thickness.

Of particular interest is that significant increases in physical properties can be achieved with a single layer of material. Prior art ePTFE has historically required laminated technology, including concentric layers of tubes or radial reinforcement from spiral-wrapped PTFE tape or similar materials, to provide sufficient strength characteristics. One distinct advantage that a single layer graft possesses over a laminated graft is that additional shape manipulation can be performed on the single layer to provide a tube of varying diameter, including a tube that is tapered or stepped. For instance, a stepped tube having the unique physical properties disclosed herein can be manufactured by manipulating a uniform diameter tube made according to the present invention over a stepped mandrel and performing an additional heating cycle at a temperature above the crystalline melt point to set the final dimensions.

Another important advantage that is provided by the HDM material of the present invention is that certain physical properties can be designed into the material through manipulation of either the radial expansion step or the calendering step. Intuitively, one skilled in the art can appreciate that altering the amount of radial expansion has a direct affect on the wall thickness of the resulting structure as well as the strength characteristics. On the other hand, it is not as apparent how the calendering step can be utilized to create structures with varying densities. The varying densities can be created along a length of a tube, for example, by employing a calendering mandrel with contours provided on its outer surface that is in contact with the tube. By calendering the tube using the methods demonstrated herein, the contours of the mandrel impart a pattern or patterns to the processed tube. These patterns result in varying densities along the length of the graft and can be designed to include features such as strain relief sections or fold lines. In addition, the patterns can impart sections that are more dense than adjacent sections for purposes such as suturing. Moreover, more dense sections can be designated to facilitate handling of the material by the user. Thus, by creating more dense sections in areas where the material will be utilized differently, the overall graft performance is enhanced.

Another variation and resulting advantage in a single layer tubular graft made according to the present invention occurs when the optional step of radial expansion is omitted. Material that is not subjected to radial dilation can be manufactured to be significantly stronger, more dense, and more rigid than similar radially expanded material. Thus, ePTFE can be manufactured to create a structure substantially rigid enough to perform functions similar to a percutaneous catheter or introducer sleeve.

As mentioned, the walls of any ePTFE structure processed according to the methods of this invention are extremely thin. Thus, the overall profile of a device in which a HDM ePTFE tubular graft is incorporated is instantly minimized. This is an important consideration given the very small areas in which an implantable device must be delivered through. Having a significantly smaller profile enables the physician to more easily navigate the device to its intended destination and provides less trauma for the patient.

Moreover, once implanted, a device incorporating the HDM ePTFE takes up less space inside the vessel, which is advantageous to blood flow. Accordingly, one of the primary uses for the HDM ePTFE is to line a support layer such as a stent for use as an endoluminal prosthesis.

The present invention additionally allows for particulate loading of filler agents into the ePTFE structure. These filler agents can consist of various biologically compatible materials that have a wide range of uses including activated carbon, antimicrobial substances, collagen, colorants, radioactive agents and radiopaque contrasting agents. Substantial concentrations can be added to the ePTFE, using methods such as those disclosed in U.S. Pat. No. 5,827,327, which is incorporated by reference. The addition of such large concentrations of filler agents in prior art ePTFE would create a substantially weaker material. However, by using the techniques of the present invention to process the ePTFE after the filler agents have been added, an ePTFE material with significant biological additives can be produced without sacrificing the strength of the material.

The present invention has been described above in terms of certain preferred embodiments so that an understanding of the present invention can be conveyed. However, there are many alternative arrangements not specifically described herein, but with which the present invention is applicable. Although specific features have been provided, the present invention would equally be embodied by other configurations not specifically recited herein. The scope of the present invention should therefore not be limited by the embodiments illustrated, but rather it should be understood that the present invention has wide applicability with respect to high density materials. All modifications, variations, or equivalent elements and implementations that are within the scope of the appended claims should therefore be considered within the scope of the invention.

What is claimed as new and desired to be protected by Letters Patent of the United States is:

1. A method for producing a high density microwall (HDM) expanded polytetrafluoroethylene (ePTFE) structure, comprising the steps of:

providing an ePTFE tube having a first inner diameter;

radially expanding said ePTFE tube to form a radially expanded tube having a second inner diameter greater than said first inner diameter;

calendering said radially expanded tube while maintaining said second inner diameter substantially constant to form a calendered tube; and heating said calendered tube above the crystalline meltpoint for polytetrafluoroethylene while maintaining said second inner diameter substantially constant to form said HDM ePTFE structure, wherein said calendering step further comprises the steps of:

positioning said radially expanded tube over a cylindrical mandrel having an outer diameter approximately equal to said second inner diameter to form a loaded mandrel;

placing said loaded mandrel between a first metallic plate and a second metallic plate, wherein said first metallic plate is maintained in a substantially parallel position with respect to said second metallic plate;

applying a force to said first metallic plate, wherein said loaded mandrel is compressed between said first and second metallic plates, and wherein said radially expanded tube is contacted by both of said first and second metallic plates during the applying step; and moving said second metallic plate in reciprocal fashion along a direction perpendicular to the central axis of said loaded mandrel while said first plate is held stationary under a constant load.

2. The method according to claim 1, wherein said radially expanding step comprises radially expanding said ePTFE tube such that said second inner diameter is approximately four times greater than said first inner diameter.

3. The method according to claim 1, wherein said calendering step further comprises a step of creating, along a length of said radially expanded tube, at least one section having a different density than an adjacent section.

4. The method according to claim 1, further comprising a step of manipulating said HDM ePTFE structure to form at least two different inner diameters along a length thereof.

5. The method according to claim 1, further comprising a step of loading a filler agent into said ePTFE tube.

6. The method according to claim 1, wherein said placing step further comprises placing a sheet of material between said loaded mandrel and at least one of said first and second metallic plates.

7. The method according to claim 1, wherein said placing step further comprises placing a sheet of material between said loaded mandrel and bath of said first and second metallic plates.

8. The method according to claim 1, wherein the radially expanding step comprises positioning the ePTFE tube in a restraining tube set at a predetermined diameter.

9. A method for producing a high density microwall (HDM) expanded polytetrafluoroethylene (ePTFE) structure, comprising the steps of:
  providing a non-radially expanded ePTFE tube having an extruded first inner diameter;
  calendering said ePTFE tube while maintaining said first inner diameter substantially constant to form a calendered tube; and
  heating said calendered tube above the crystalline melt-point for polytetrafluoroethylene while maintaining said first inner diameter substantially constant to form said HDM ePTFE structure, wherein said calendering step further comprises the steps of:
  positioning said ePTFE tube over a cylindrical mandrel having an outer diameter approximately equal to said first inner diameter to form a loaded mandrel;
  placing said loaded mandrel between a first metallic plate and a second metallic plate, wherein said first metallic plate is maintained in a substantially parallel position with respect to said second metallic plate;
  applying a force to said first metallic plate, wherein said loaded mandrel is compressed between said first and second metallic plates, and wherein said non-radially expanded tube is contacted by both of said first and second metallic plates during the applying step; and
  moving said second metallic plate in reciprocal fashion along a direction perpendicular to the central axis of said loaded mandrel while said first plate is held stationary under a constant load.

10. The method according to claim 9, wherein said calendering step further comprises a step of creating, along a length of said non-radially expanded tube, at least one section having a different density than an adjacent section.

11. The method according to claim 9, further comprising a step of manipulating said HDM ePTFE structure to form at least two different inner diameters along a length thereof.

12. The method according to claim 9, further comprising a step of loading a filler agent into said ePTFE tube.

13. The method according to claim 9, wherein said placing step further comprises placing a sheet of material between said loaded mandrel and at least one of said first and second metallic plates.

14. The method according to claim 9, wherein said placing step further comprises placing a sheet of material between said loaded mandrel and both of said first and second metallic plates.

* * * * *